United States Patent

Csongor et al.

[11] Patent Number: 5,932,154
[45] Date of Patent: *Aug. 3, 1999

[54] PROCESS OF MAKING A PLASTIC PART WITH A RETROFITTED SCREW MACHINE

[76] Inventors: Desi G. Csongor, 19 Bennett St.; Donald N. Halgren, 35 Central St., both of Manchester, Mass. 01944

[ * ] Notice: This patent is subject to a terminal disclaimer.

[21] Appl. No.: 08/858,955

[22] Filed: May 20, 1997

Related U.S. Application Data

[63] Continuation-in-part of application No. 08/773,875, Dec. 30, 1996, Pat. No. 5,744,092, which is a continuation-in-part of application No. 08/511,055, Aug. 3, 1995, Pat. No. 5,670,112, which is a continuation-in-part of application No. 08/393,200, Feb. 23, 1995, abandoned.

[51] Int. Cl.$^6$ .............................. B29C 45/76; B29D 22/00
[52] U.S. Cl. ............................ 264/40.3; 29/592; 264/572; 408/1 R
[58] Field of Search .................................. 264/40.3, 572; 29/592; 408/1 R

[56] References Cited

U.S. PATENT DOCUMENTS

| 3,387,331 | 6/1968 | Billings | 425/192 R |
| 3,902,704 | 9/1975 | Ishibashi et al. | 366/79 |
| 4,174,935 | 11/1979 | Driskill | 425/113 |

*Primary Examiner*—Leo B. Tentoni
*Attorney, Agent, or Firm*—Don Halgren

[57] ABSTRACT

The invention includes retrofitting a plasticating machine for the working and forcing of plastic material into a moldor die, the machine including an elongated housing having a first or proximal end and a second or distal end, and elongated screw shaft with a screw flight therearound. The screw shaft is rotatably supported in the elongated housing, for the working of plastic between the screw shaft and the elongated housing with at least one delivery conduit generally longitudinally arranged through the screw shaft, from a location proximal to the distal tip end of the screw. To accomplish such delivery, the screw shaft is replaced with a corresponding screw shaft with a bore extending through the distal tip end thereof, or the existing screw shaft is machined to have such a bore extend therethrough, from location proximal to the distal end out through the distal tip end. The bore in one embodiment may extend completely through the screw shaft, from its proximalmost end to its distalmost tip end. The conduit may be arranged to be movable in the bore, with respect to the screw shaft to permit delivery of a medium through the screw shaft to any plastic being worked by the machine. The medium may be any single or combination of components selected from the group comprising vapor, liquid, gas, powder or solid, to control the machine or treat any plastic being worked therefrom.

7 Claims, 2 Drawing Sheets

PROCESS OF MAKING A PLASTIC PART WITH A RETROFITTED SCREW MACHINE

The present invention relates to an arrangement for retrofitting screw machines for molding products from a plastic material, this Application being a Continuation-In-Part Application of U.S. patent application Ser. No. 08/773,875 now U.S. Pat. No. 5,744,092, filed Dec. 30, 1996 which is a Continuation-In-Part of U.S. patent application Ser. No. 08/511,055, filed Aug. 3, 1995 now U.S. Pat. No. 5,670,112 which is a Continuation-In-Part Application of U.S. application Ser. No. 08/393,200, filed Feb. 23, 1995, now abandoned each of which are incorporated herein by reference.

BACKGROUND OF THE INVENTION

1. Field of the Invention

This invention relates to plastic processing machines, and more particularly to retrofitting plasticating screw machines with bored out screw arrangements for extrusion and injection molding.

2. Prior Art

Injection molding and extrusion employs the steps of hot working a plasticized or melted thermoplastic material and forcing same under high pressure into a mold or mold space, then allowing the material to cool sufficiently so that it hardens to the extent that it can retain its shape after removal from the mold or as it emanates from the mold.

During the plasticating process, it is often desirable to add a further processed material with the plastic material being worked within a screw housing. It is further desired to be able to add a solid, such as a pellet, wire, gas or a vapor, into the actual plastic material being molded or extruded.

Limitations of present plasticating screw machinery prevent the simultaneous introduction of a gas and/or a liquid, and or a vapor, and/or a solid, into that thermoplastic material as it is going into a mold or die.

It is therefore an object of the present invention, to provide a modification to plasticating screw machines so they may have capabilities not found in the prior art.

It is a further object of the present invention, to enable a screw machine to present a solid and/or a liquid, and/or a vapor, and/or a gas, through its screw, simultaneously or sequentially into a plastic being molded and/or extruded.

It is yet a further object of the present invention, to enable a plasticating screw machine to permit the rapid cooling and completion of a plastic part in a manner not found in the prior art.

It is yet still a further object of the present invention, to provide an extrusion and/or injection molding screw with multiple capabilities to be retrofitted into a plasticating screw machine to enable it to mix and/or extrude and/or mold multiple components therewith in a manner not found in the prior art.

BRIEF SUMMARY OF THE INVENTION

The present invention relates to an arrangement for retrofitting plasticating screw machines to enable them to treat thermoplastic material and pressurizably direct that thermoplastic material into an extrusion die or into an injection mold.

Retrofitting plasticating screw machines according to the present invention comprises removing the prior art screw from the external barrel shaped housing in which it is supported. The screw shaft may then be machined to contain an elongated bore therethrough according to the principles of the present invention, or the prior art screw may be replaced by comparable, previously machined screw which is utilized to replace the previous screw. The housing and the replacement or retrofitted screw shaft have a proximal or first end and a distal or a second end. The retrofuitted screw shaft is rotatively empowered at the proximal first end of the housing by a motor drive means thereattached. At least one material in-feed supply hopper may be arranged through the housing near the proximal end thereof.

The retrofitted screw shaft may be machined to have a bore extending along its longitudinal axis, from a location proximal to its distalmost end, or in a further embodiment, all the way through from its proximalmost end to its distal tip end. The bore has a wall surface which may be rifled, that is, has a spiral groove cut within its surface, to define a material moving path.

A non-rotational sleeve support may be arranged within the bore of the retrofitted screw shaft, extending preferably from at or near the proximal end of the housing, to the distal end of the shaft. A plurality of conduits may be retrofittably arranged within the sleeve support within the bore of the retrofitted screw shaft. In one embodiment, the conduits preferably extend out from the proximal end of the sleeve support, the conduits being in communication with any medium(s) such as a gas source, a vapor source, a liquid source, a powder or solid source for feeding wire, pellets, powder, cooling fluid or the like into those conduits. The conduits have a distalmost end within the distal end of the screw shaft. The conduits may be held within a support baffle at the distal end of the sleeve. The sleeve support may be held in a bearing arranged within the walls of the bore of the replacement or retrofitted screw shaft adjacent its distal end, for supportive carrying therein.

Each of the conduits may be arranged to be moved longitudinally with respect to the retrofitted screw shaft and or the sleeve support within the bore to advance its respective discharge end into any thermoplastic material as it emanates from the distal end of the housing. One or more of the conduits may be longitudinally advanceable through an opening or a mold die at the end of the housing, or into a injection mold at the distal end of the housing. The sleeve support may comprises a tubular member which encircles the conduit(s).

In a further preferred embodiment of the present invention, the entire sleeve support arrangement within the bore of the retrofitted or replacement screw shaft may be longitudinally advanceable through the distal end of the housing, so as to present the delivery of any combination of medium(s) such as fluids, gas, vapors, and or solids such as wires, reinforcement fibers, optical glass and/or plastic at any location in or downstream of the plasticating screw and/or within the plastic being processed during the plasticating operation. Such medium(s) may permit the "through the screw" cooling, reinforcement, electrifying, lighting, softening, hardening, gasifying, hollowing or densification of any plastic being extruded or injected from the plasticating screw machine. Some exemplary products are: telephone poles, light poles, railroad ties, plastic lumber, timber, automobile components, bumpers, fenders, dashboards, office products, electrical equipment, structural components with or without cores therein, or the like.

A further preferred embodiment contemplates a transfer of melted or fluid material along the annular path between a non rotatable sleeve support and the rifled wall of the bore within the retrofitted or replacement screw shaft, to provide yet a further annular mixing chamber to the plasticating chamber between the flights of the improved elongated screw and the inner walls of the housing enclosing and supporting the elongated screw shaft.

A yet further preferred embodiment of the present invention contemplates the sleeve being rotatively disposed within the bore of the improved elongated screw shaft, either in a rotating or counter-rotating manner depending upon the direction of rotation of the improved elongated screw shaft itself. Such a rotating sleeve, would have a drive mechanism at its proximal end, in conjunction with a longitudinal displacement mechanism for advancing and retracting the sleeve longitudinally within the bore of the improved retrofitted or replacement screw shaft, in a manner to permit any conduit therewithin to deliver and/or withdraw any single or combination of medium partway or completely through the distal end of the improved elongated screw shaft and or plastic being extruded and/or ejected from said screw and into a mold at the distal end of the plasticating screw machine.

In still yet a further embodiment of the present invention, when the improved retrofitted or replacement screw shaft and its retrofitted associated internal conduits therethrough are used in an injection molding operation, a mold may be utilized having an "inarticle" pin therewithin. The inarticle pin may be utilized to further supply and/or evacuate gas or liquids and/or powder from the injection mold. The inarticle pin may be retractably arranged within the mold, by a piston mechanism, which will move the pin from the mold itself. A fluid supply and vacuum line is in communication with the hollow inarticle pin and is in communication with a supply and discharge source, to permit such injection mold with a supply and vacuum means thereat.

Thus there has been shown, a unique retrofittable or replacement screw construction for an injection molding machine or a plastic extrusion machine, wherein that same improved retrofitted or replacement screw has a plurality of function transfer means included therewith. The separate conduits in the retrofitted or replacement screw may be utilized individually or in combination, to continuously or sequentially add or withdraw a medium such as a vapor, a gas, a liquid, a foam, or a solid, into a plasticated material going into or through a die or a mold. The multiple conduits may be utilized to duct rearwardly excess gas, or vapor, or foam or liquid, or cooling material from the bore of the improved elongated screw shaft and/or support sleeve and/or tubular member therethrough, or mold, in conjunction with an inarticle pin arrangement or by themselves. If the improved screw shaft were to be used in the plastic injection format, the screw itself could be longitudinally advanceable and retractable towards a mold form.

The invention thus comprises an improved plasticating machine for the working and forcing of plastic material into a mold, said machine including an elongated housing having a first or proximal end and a second or proximal end, with a retrofitted or replacement screw shaft with a screw flight therearound, the screw shaft being rotatably supported in the elongated housing, for the working of plastic between the screw shaft and the elongated housing, at least one delivery conduit generally longitudinally arranged through the improved screw shaft, from a proximal end to a distal tip end thereof, the conduit arranged to be movable with respect to the improved retrofitted or replacement screw shaft to permit delivery of a medium through the improved screw shaft to any plastic being driven from the machine. The medium may be any single or combination of components selected from the group comprising vapor, liquid, gas, powder or solid.

The retrofitted delivery conduit is arranged so as to be movable longitudinally with respect to the machined-out bore in the improved elongated screw shaft. The delivery conduit is supported within a conduit support within the bore through the elongated screw shaft. The delivery conduit has a supply duct arranged on its proximal end, to supply said medium to the conduit for distribution of the medium into any plastic being delivered to a mold adjacent the distal end of the screw shaft. The conduit support may enclose a plurality of conduits therein, for the supply of a plurality of mediums to any plastic being delivered to a mold adjacent said distal end of the improved screw shaft. Each of the conduits in the plurality of conduits may be arranged parallel to one another. Each of the conduits in the plurality of conduits may be arranged coaxial with one another. At least one of the conduits may be arranged to carry a vacuum, to return a medium from the distal end of the conduit extending distally from the improved screw shaft to the proximal end thereof. The conduit support may comprise an elongated sleeve. The elongated sleeve may be movable with respect to the improved elongated screw shaft. The improved elongated screw shaft may include a central bore machined therethrough from a proximal end to a distal tip end thereof, which central bore may have a grooved rifling machined therethrough, to assist in the movement of any medium passing through the bore itself. At least one of the retrofitted conduits may be arranged to carry a cooling fluid therethrough, so as to provide a temperature control to any medium traveling thereadjacent. The improved elongated screw shaft may be movable longitudinally with respect to the "original" elongated housing in which it is supported, to allow injection of plastic material from the housing into a mold thereadjacent. The mold may comprise a hollow injection mold. The retrofitted conduits may be longitudinally advanceable and retractable with respect to the mold, to permit a medium to be delivered to or into and/or withdrawn from any plastic supplied to the mold.

The invention also comprises a method of supplying a plastic to a mold or a die for the manufacture of a plastic part therefrom, including the steps of providing an elongated rotatable screw shaft within an elongated barrel housing, the housing having a mold or die adjacent a distal end thereof, machining a longitudinally directed bore through the elongated screw shaft from a location proximal of a distal end thereof, fitting at least one delivery conduit through the bore, so as to permit a medium to be directed through the screw shaft to any plastic being delivered to the mold or die adjacent the distal end of the housing, and attaching a medium supply duct at the proximal end of the conduit to permit a medium to be delivered through the conduit through the screw shaft and to a plastic part being generated at the distal end of the housing. The method may include the step of axially moving the delivery conduit longitudinally with respect to the improved screw shaft, to permit controlled delivery of the longitudinal location of any medium with respect to the improved screw shaft and the mold or die thereadjacent. The method may include the step of retrofitting a plurality of conduits within the bore of the improved elongated screw shaft, to permit the delivery of a plurality of mediums therethrough, to allow any plastic driven from the housing to be mixed with and/or treated by the mediums. The method may include the step of supplying any medium to the proximal end of the conduits, selected from the group comprising: a vapor, a cooling gas, a heated gas, a liquid, an optical fiber, a reinforcing fiber, an electrical conductor, and electrical resistor.

BRIEF DESCRIPTION OF THE DRAWINGS

The objects and advantages of the present invention, will become more apparent, when viewed in conjunction with the following drawings, in which.

DESCRIPTION OF THE PREFERRED EMBODIMENTS

Figure 1:
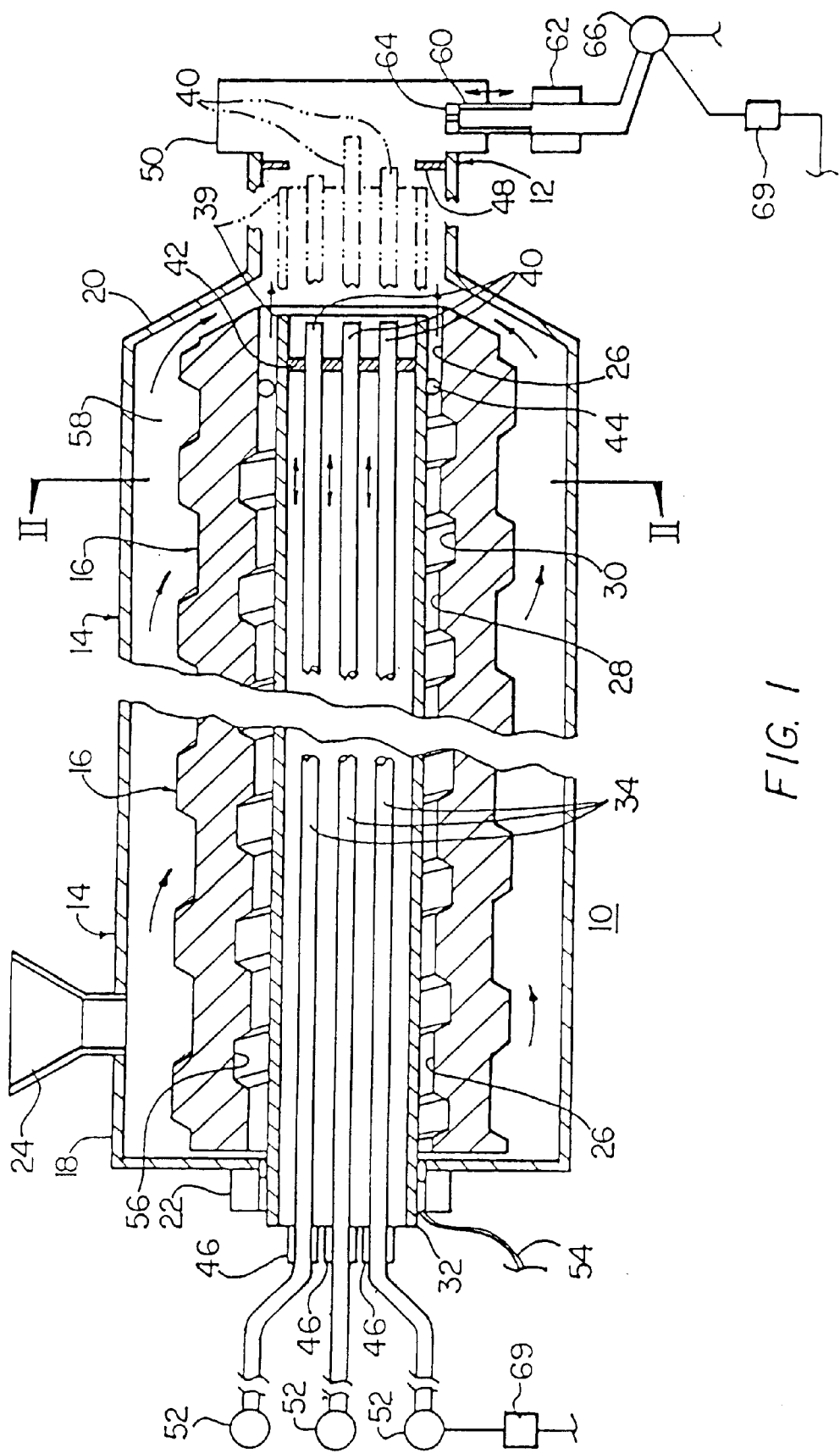
FIG. 1 is a side elevational view, in section, showing a plasticating screw shaft retrofitted with a bore and multiple conduit assembly therewithin for treatment of thermoplastic material, according to the principles of the present invention.
Figure 2:
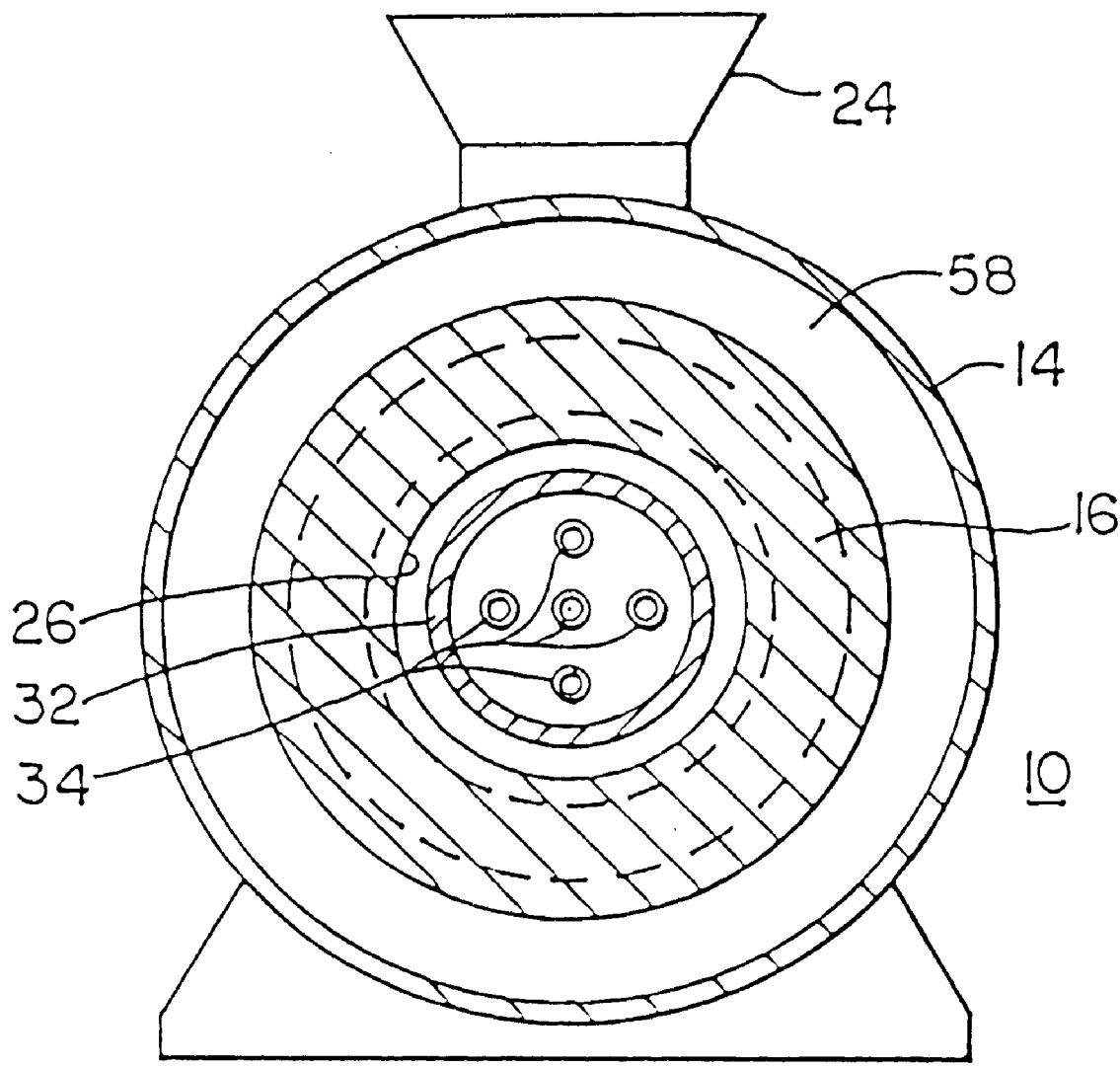
FIG. 2 is a view taken along the lines 2—2 of FIG. 1.

Referring now to the drawings in detail, and particularly to FIGS. 1 and 2, there is shown the present invention which relates to retrofitting a plasticating screw machine 10 to enable it to be useful for treating of thermoplastic material and pressurizably directing that thermoplastic material into an extrusion die or into an injection mold 12 thereadjacent.

The retrofitted improved plasticating screw machine 10 of the present invention comprises an external barrel shaped housing 14 having an elongated screw shaft 16 rotatively supported therewithin. The housing 14 and the screw shaft 16 have a proximal or first end 18 and a distal or a second end 20. The screw shaft 16 is rotatively empowered at the proximal first end 18 of the housing 14 by a motor drive means 22 thereattached. At least one material in-feed supply hopper 24 may be arranged through the housing 14 near the proximal end 18 thereof.

The screw shaft 16 has been improved by being machined to have a bore 26 extending completely therethrough along its longitudinal axis, from its proximalmost end to its distalmost end. The bore 26 has a wall surface 28 which may be rifled, that is, has a spiral groove 30 cut within its surface, to define a further material moving path.

A non-rotational sleeve support 32 may be retrofittably arranged within the bore 26 of the screw shaft 16, extending preferably from the proximal end 18 of the housing 14, to the distal end 20 of the screw shaft 16. A plurality of conduits 34 may arranged within the sleeve support 32 within the bore 26 of the screw shaft 16. The conduits 34, in one embodiment, preferably extend outwardly from the proximal end of the sleeve support 32, the conduits 34 being arranged to be in communication with any medium(s) such as a gas source, a vapor source, a liquid source, a powder or solid source (for feeding wire, pellets, powder, an optical cable, an electrical conductor, an electrical resistance device or the like), cooling or heating fluid or the like into those conduits 34. The conduits 34 have a distalmost end 40 within the distal end 20 of the improved screw shaft 16. The conduits 34 may be held within a support baffle 42 at the distal end of the sleeve support 32. The sleeve support 32 may be held in a bearing 44 arranged within the walls 28 of the bore 26 of the improved screw shaft 16 adjacent its distal end, for supportive carrying therein.

Each of the conduits 34 may also be moved longitudinally with respect to the improved screw shaft 16 by a displacement gear 46 or the like, and or moving the entire sleeve support 32 within the bore 26 to advance its respective discharge end 39 into any thermoplastic material as it emanates from the distal end 20 of the housing 14. One or more of the conduits 34 may be longitudinally advanceable through a die 48 at the downstream end of the housing 14, or into an injection mold 50 at the distal end of the housing 14, the molds 48 and 50 (shown together for exemplary purposes). The sleeve support 32 may comprise a tubular member which completely longitudinally encircles the conduit(s).

In a further preferred embodiment of the present invention, the entire retrofitted sleeve support 32 within the bore 26 of the improved screw shaft 16 may be longitudinally advanceable through the distal end 20 of the housing 14, so as to present the delivery of any combination of medium(s) such as fluids, gas, vapors, and or solids such as wires, reinforcement fibers (fiber glass), optical glass and/or plastic from a source 52 at the proximal end of the machine 10, so as to provide medium(s) at any location in or downstream of the improved plasticating screw 16 and/or within the plastic being processed during the plasticating operation. Such medium(s) may permit the cooling, reinforcement, electrifying, lighting, softening, hardening, gasifying, hollowing or densification of any plastic being extruded or injected from the plasticating screw machine 10.

A further preferred embodiment contemplates a transfer of melted or fluid material from a source 54, along the annular path 56 between the non-rotatable sleeve support 32 and the rifled wall 28 of the bore 26 within the improved retrofitted screw shaft 16, to provide yet a further annular mixing chamber in addition to the plasticating chamber 58 between the flights of the elongated screw shaft 16 and the inner walls of the housing 14 enclosing and supporting the elongated screw shaft 16.

A yet further preferred embodiment of the present invention contemplates the retrofitted support sleeve 32 being rotatively disposed within the bore 26 of the elongated screw shaft 16, either in a rotating or a counter-rotating manner depending upon the direction of rotation of the elongated screw shaft 16 itself. Such a rotating sleeve 32, would have a drive mechanism (not shown for simplicity of figures), at its proximal end, in conjunction with a longitudinal displacement mechanism (also not shown for simplicity of figures) for advancing and retracting the sleeve 32 longitudinally within the bore 26 of the improved screw shaft 16, in a manner to permit any conduit 34 therewithin to deliver and/or withdraw any single or combination of medium completely through or partway the elongated screw shaft 16, and or plastic being extruded and/or ejected from said screw shaft 16 and into a die or mold 12 at the distal end of the plasticating screw machine 10.

In still yet a further embodiment of the present invention, when the retrofitted improved screw shaft 16 and associated internal conduits 34 therethrough, are used in an injection molding operation, the injection mold 50 may be utilized having an "inarticle" pin 60 therewithin. The inarticle pin 60 may be utilized to further supply and/or evacuate gas or liquids and/or powder from the injection mold 50. The inarticle pin 60 may be retractably arranged within the mold 50, by a piston or like mechanism 62, which will move the pin 60 into and from the mold 50 itself. The pin 60 may have a jeweled orifice 64 at its inner end to minimize wear and hence prolong the life of such a pin 60. A fluid supply and vacuum line 66 is in communication with the hollow inarticle pin 60 and is in communication with the supply and discharge source 66, to permit such injection mold 50 with a supply and vacuum means thereat.

Thus there has been shown, a unique improved screw construction for an injection molding machine or a plastic extrusion machine, wherein that same screw may be retrofitted to have a plurality of function transfer means included therewith. The separate conduits may be utilized individually or in combination, to continuously or sequentially add or withdraw a medium such as a vapor, a gas, a liquid, a foam, or a solid, into a plasticated material going into or through a die or a mold. The single/multiple stationary/axially movable or rotatable conduits may be utilized to duct rearwardly excess gas, or vapor, or foam or liquid, or cooling material from the bore of the improved elongated screw shaft and/or support sleeve and/or tubular member therethrough, or mold, in conjunction with an inarticle pin arrangement or by themselves, which may all be regulated by a proper electronic control circuit 69 communicating with the conduit and sleeve moving apparatus, the medium sources and the pin for regulating quantity, temperature, pressure and distance. If the improved retrofitted screw shaft were to be used in the plastic injection format, the screw itself could be longitudinally advanceable and retractable towards a mold form.

We claim:

1. A method of supplying a plastic from a retrofitted plasticating screw machine to a mold or die for the manufacture of a plastic part therefrom, comprising the steps of:

providing an elongated rotatable screw shaft within an elongated barrel housing, said housing having a mold or die adjacent a distal end thereof;

machining a longitudinally directed bore through said elongated screw shaft from a location proximal of a distal tip end through said distal tip end thereof to permit said screw shaft to be retrofitted;

fitting at least one delivery conduit to said bore, so as to permit a medium to be directed through said retrofitted screw shaft to any plastic being delivered to said mold or die adjacent said distal end of said housing;

attaching a medium supply duct to a proximal end of said bore to permit a medium to be delivered to said bore and through said distal tip end of said bore in said retrofitted screw shaft and to a plastic being worked at said distal end of said screw shaft; and supplying a plastic to said mold or die from said screw machine.

2. The method of supplying a plastic from a retrofitted plasticating screw machine to a mold or die for the manufacture of a plastic part therefrom, as recited in claim 1, comprising the steps of:

fitting at least one delivery conduit through said bore, so as to permit a medium to be directed through said retrofitted screw shaft to any plastic being delivered to said mold or die adjacent said distal end of said housing; and attaching a medium supply duct to a proximal end of said conduit to permit a medium to be delivered through said conduit and through said distal tip end of said retrofitted screw shaft and to a plastic being worked at said distal end of said screw shaft.

3. The method as recited in claim 2, including the step of:

moving said delivery conduit longitudinally with respect to said screw shaft, to permit controlled delivery of the longitudinal location of any medium with respect to said screw shaft.

4. The method as recited in claim 3, including the step of:

arranging a plurality of conduits within said bore of said screw shaft, to permit the delivery of a plurality of mediums therethrough, to allow any plastic driven from said housing to be treated by said mediums.

5. The method as recited in claim 4, including the step of:

supplying any medium to said proximal end of said conduits, selected from the group consisting of: a vapor, a cooling gas, a heated gas, a liquid, an optical fiber, a reinforcing fiber, an electrical conductor, and electrical resistor.

6. The method as recited in claim 1, including the step of:

placing an inarticle pin into said mold to supply or evacuate a medium therefrom, said inarticle pin having a conduit arranged therewith to provide such supply or evacuation process thereto.

7. The method as recited in claim 5, including the step of:

controlling the timing of the use of said inarticle pin to the supply of medium passing into said plastic in said mold through said delivery conduit, by a control circuit connected therebetween.

\* \* \* \* \*